(12) United States Patent
Eshet

(10) Patent No.: US 12,102,476 B2
(45) Date of Patent: Oct. 1, 2024

(54) CONTACT-FREE ACOUSTIC MONITORING AND MEASUREMENT SYSTEM

(71) Applicant: Omer Eshet, Kibbutz Einat (IL)

(72) Inventor: Omer Eshet, Kibbutz Einat (IL)

( * ) Notice: Subject to any disclaimer, the term of this patent is extended or adjusted under 35 U.S.C. 154(b) by 416 days.

(21) Appl. No.: 17/646,502

(22) Filed: Dec. 30, 2021

(65) Prior Publication Data

US 2022/0192628 A1 Jun. 23, 2022

Related U.S. Application Data

(63) Continuation-in-part of application No. PCT/IL2020/050721, filed on Jun. 28, 2020.

(30) Foreign Application Priority Data

Jul. 1, 2019 (IL) .......................................... 267774

(51) Int. Cl.
*A61B 8/08* (2006.01)

(52) U.S. Cl.
CPC .......... *A61B 8/0883* (2013.01); *A61B 8/5276* (2013.01)

(58) Field of Classification Search
CPC ....... A61B 8/0883; A61B 8/5276; A61B 8/52; A61B 8/488; A61B 8/08; A61B 5/021; A61B 5/0816; A61B 5/0077; A61B 5/1114; A61B 5/7207; A61B 5/7465; A61B 5/02405; A61B 5/08; A61B 5/103;

(Continued)

(56) References Cited

U.S. PATENT DOCUMENTS

| 4,985,925 A | 1/1991 | Langberg et al. |
| 5,590,650 A | 1/1997 | Genova |
| 9,462,994 B2 | 10/2016 | Rogers et al. |

(Continued)

FOREIGN PATENT DOCUMENTS

| WO | 2018/015638 A1 | 1/2018 |
| WO | 2019/026076 A1 | 2/2019 |

OTHER PUBLICATIONS

Arlotto et al. "An Ultrasonic Contactless Sensor for Breathing Monitoring", Sensors, 2014, vol. 14, No. 8, pp. 15371-15386.

(Continued)

*Primary Examiner* — Boniface N Nganga
(74) *Attorney, Agent, or Firm* — Vorys, Sater, Seymour and Pease LLP; Anthony P. Venturino; Maryellen Feehery Hank

(57) ABSTRACT

The present disclosure concerns a system for determining vital signs of a subject, such as heart activity profile (e.g. heart rate and heart rate variability), respiration rate or blood pressure. The above vital signs can be extracted from analyzing the movement profile of the chest due to heartbeat, e.g. ballistocardiography (BCG), and respiration process.
The monitoring system processes and analyzes measured data of acoustic signals that are obtained by transmitting acoustic signals, in particular, ultrasonic signals, towards a subject and detecting the reflected signals therefrom. The transducer/transmitter of the acoustic signals is positioned remotely from the subject such that the signal communication between the measured subject and the transducer is contact-free. The analysis includes determining a variation profile of phase and frequency between the transmitted signals and the reflections thereof from the subject, and said variation profile is indicative of vital signs of the subject.

20 Claims, 13 Drawing Sheets

(58) Field of Classification Search
CPC . A61B 5/11; A61B 5/1102; A61B 2562/0219; G01S 15/36; G01S 15/50
See application file for complete search history.

(56) References Cited

U.S. PATENT DOCUMENTS

| | | |
|---|---|---|
| 2012/0283581 A1 | 11/2012 | Olde et al. |
| 2013/0060100 A1 | 3/2013 | Wurm et al. |
| 2019/0076129 A1 | 3/2019 | Ward, III et al. |
| 2019/0099156 A1 | 4/2019 | Bocca et al. |

OTHER PUBLICATIONS

Denenberg, "Anti-noise", IEEE Potentials, 1992, vol. 11, No. 2, pp. 36-40.

Pinheiro et al., "Theory and Developments in an Unobtrusive Cardiovascular System Representation: Ballistocardiography", The Open Biomedical Engineering Journal, 2010, vol. 4, pp. 201-216.

734

CONTACT-FREE ACOUSTIC MONITORING AND MEASUREMENT SYSTEM

TECHNOLOGICAL FIELD

This invention is in the field of vital signs monitoring and measurement using acoustic signals.

BACKGROUND ART

References considered to be relevant as background to the presently disclosed subject matter are listed below:

Pinheiro, Eduardo, Octavian Postolache, and Pedro Girão. "Theory and developments in an unobtrusive cardiovascular system representation: ballistocardiography." *The open biomedical engineering journal* 4 (2010): 201.

Arlotto, Philippe, et al. "An ultrasonic contactless sensor for breathing monitoring." *Sensors* 14.8 (2014): 15371-15386.

Acknowledgement of the above references herein is not to be inferred as meaning that these are in any way relevant to the patentability of the presently disclosed subject matter.

BACKGROUND

Vital signs of human beings, such as heart rate, heart rate variability, respiration rate or blood pressure, may reflect on the physical condition thereof. For example, when a human gets sick, it may be manifested in its vital signs. In today's world, when automated machines may have a direct influence on humans, it may be of value to provide these machines data indicative of the vital signs of a subject so they can react accordingly.

To this end, there is a need for a solution that will provide such monitoring without interrupting and limiting the everyday life activities.

General Description

The present disclosure concerns a system for determining vital signs of a subject, such as heart activity profile (e.g. heart rate and heart rate variability), respiration rate or blood pressure. The above vital signs can be extracted from analyzing the movement profile of the chest due to heartbeat, e.g. ballistocardiography (BCG), and respiration process.

The monitoring system, more specifically a control unit thereof, processes and analyzes measured data of acoustic signals that are obtained by transmitting acoustic signals, in particular, ultrasonic signals, towards a subject and detecting the reflected signals therefrom. The transducer/transmitter of the acoustic signals is positioned remotely from the subject such that the signal communication between the measured subject and the transducer is contact-free. The analysis includes determining a variation profile of phase and frequency between the transmitted signals and the reflections thereof from the subject, and said variation profile is indicative of vital signs of the subject.

Thus, the monitoring system of the present disclosure comprising a control system configured for data communication with an acoustic device to receive measured data indicative of reflection of predetermined acoustic signals from the subject. More specifically, the measured data is indicative of reflection of predetermined acoustic signals that are reflected substantially from the external surface of the subject, namely the external shape thereof. The reflected signals may comprise data indicative of the movement of the external surface, e.g. a general movement of the subject or the movement of the surface of the skin due to heartbeat. The control system comprising an analyzer module configured and operable to analyze the measured data and determine a variation profile of at least one of the phase (time) and frequency between the predetermined acoustic signal and the reflection thereof from the subject. The control unit is in data communication with an extractor module configured and operable to extract data indicative of the vital signs profile of the subject from said variation profile data. In some embodiments, the extractor is comprised within the control unit. In other embodiments, the extractor may be external to the control unit.

The monitoring system can include the measurement device that provides the measurement data. Such a measurement device can be an acoustic device comprising at least one transceiver unit that is configured and operable to remotely transmit acoustic signals towards the region of interest, namely the measured subject. In other words, the acoustic device operates in contact-free signal communication with the subject, and the generated signals therefrom propagate through the medium between the acoustic device and the subject, e.g. air, until being reflected from the subject's external surface, and propagate through the air until they are being received in the transceiver unit.

It is to be noted that in some embodiments the measured data comprises multiple measured signals, each being indicative of a variation profile data with respect to a reflection of a corresponding acoustic signal of predetermined characteristics.

In some embodiments of the monitoring system, said variation profile comprises phase variation over time, in result to a movement of the body that the signal reflected from, of the reflection of predetermined acoustic signals from the subject.

The extractor module may comprise a fitting utility that matches between the variation profile obtained from the measured data and a reference signal that is based on or associated with a predetermined theoretical data or a predetermined collected data, which are indicative to a vital sign, to determine a vital sign associated with the measured data.

In some embodiment of the monitoring system, said measured data comprises a first signal component indicative of movement associated with the BCG movements of the subject and a second signal component indicative of either body movements of the subject not associated with BCG movements or static reflections. The monitoring system further comprising a noise cancelling unit configured for: (i) determining a time window of said reflection of predetermined acoustic signals in correlation with the reference signal to define a time-windowed signal, namely the time window is having the same duration of the reference signal that is correlated by the fitting utility and therefore the phase of the signals are also correlated, the time-windowed signal is typically not varying in time and each time-windowed signal is a signal that applies only for a specific correlation time; (ii) applying a cancelation function between the time-windowed signal and the reference signal, e.g. subtracting one signal from the other, to determine a noise-residue signal; (iii) applying a tuning function between the noise-residue signal and the second signal component to determine a noise cancellation signal, e.g., passing the second signal component through a tunable filter that is tuned according to the noise-residue signal; and (iv) applying the noise cancellation signal on the first signal component to determine a noise-free signal. The analyzer module is configured and operable to analyze said noise-free signal and determine said variation profile, namely the system operates in a closed loop and the variation profile is determined based on the noise-free signal.

A database of reference signals is accessible by the monitoring system or is a part of it. The reference signals in the database are pre-obtained, namely either created based on theoretical data or pre-obtained measurements of similar acoustic signals that are labeled to represent a certain vital sign. Thus, when the fitting utility matches real-time signal with a reference signal, a vital sign is determined based on the labeling of the matching reference signal.

The monitoring system of the present disclosure may be utilized in various applications. When installed in a vehicle, it is directed to the driver or any one of the passengers to monitor vital signs during the ride. The system can identify changes or abnormalities of the vital signs and provide an alert to one of the systems of the vehicle, e.g. automated driving system or any other control system that may affect the conditions within the vehicle, such as air conditioning, or one or more driving parameters of the vehicle.

Another implementation of the system is when it is installed for continuously monitoring an infant in a crib. When the system identifies a change or abnormality of the vital sign of the infant, it is configured to output an alert. The alert can be received in a mobile device or any other device that is configured to receive the alert and display it visually or audibly.

In some embodiments, the fitting utility is configured to determine the at least one vital sign from a plurality of vital signs stored in a database.

The database stores predetermined data related to vital signs that may include many types such as theoretical models, calculated models and diagrams of predetermined measurements, etc.

The transmission of acoustic signals towards a subject results in a variation profile of the measured data that is indicative of the movement of the subject. In addition to the general movement of the subject, the variation profile data may be indicative of local movements, such as chest movements. In some embodiments, the data may be indicative of a BCG signature of the subject. This data can be identified by one or both of the analyzer and extractor module.

In order to process the measured data, the analyzer or the extractor may apply to either the measured data or the variation profile, one or more wavelet transform models. The extractor may apply other techniques to obtain the data indicative of the movement of the subject, either alone or in a combination with the wavelet transform. These techniques include, but not limited to, Fourier analysis based frequency estimation and Machine Learning (e.g. Deep Learning, Artificial Neural Network).

The monitoring system may further comprise a noise reduction system that has a noise reduction module to reduce signals coming from outside of a region of interest, such as static objects.

One technique used in the noise reduction system is to identify signals reflected from regions or objects outside of the region of interest. For example, static standing waves may indicate that the signal is reflected from a static object.

To suppress the undesired, noise, signals, the system may comprise at least one additional acoustic transceiver unit to transmit acoustic signals comprising signal components having characteristics oppositely matching characteristics of acoustic signals propagating towards the acoustic device from outside the region of interest. This will result in a destructive interference that will suppress the noise signal.

It is to be noted that the control system or at least part thereof may be remoted from the measurement or acoustic device. For example, the analysis of the control system may be performed at least partially in a remote cloud server.

In some embodiments the acoustic device comprising a control unit comprising a signal generator operating the acoustic transceiver unit, which comprises a main transceiver and a secondary transceiver, the control unit being configured and operable to process preliminary measured data obtained by the acoustic transceiver unit to identify acoustic signal components from the outside of the region of interest as signals having predetermined characteristics corresponding to reflections of acoustic radiation/signals from substantially static objects, and operating the signal generator to operate the secondary transceiver to transmit acoustic signals having characteristics oppositely matching said predetermined characteristics thereby preventing reflections of acoustic radiation/signals from substantially static objects to be received.

The acoustic device may comprise multiple receivers arranged at predetermined locations with respect to said at least one acoustic transceiver unit, the noise reduction module being configured and operable to analyze a combined output signal of said multiple receivers to thereby identify the acoustic signals from the outside of the region of interest.

The noise reduction system may comprise a cancellation module configured and operable to utilize input data indicative of characteristics of the predetermined acoustic signals and process data indicative of acoustic signals being received by applying thereto data corresponding to acoustic signals oppositely matching the characteristics of the predetermined acoustic signals.

The cancellation module may be configured either as an analog circuit for applying said processing to the acoustic signals being received by the transceiver unit or as a digital processor for applying said processing to a digital representation of the received acoustic signals.

External sensing data may be received by the monitoring system and participate in the data processing. Therefore, the monitoring system may be in data communication with at least one of (i) a motion sensor device, which is configured and operable for sensing a movement profile of the subject and generating corresponding motion data; (ii) an image acquisition device, which is configured and operable for visually monitoring a movement of the subject and generating image data indicative thereof.

The acoustic device of the monitoring system of this disclosure is configured and operable in a frequency range between 30 KHz and 5 MHz.

In another aspect of this disclosure, it is provided a system for determining vital signs profile of a subject comprising: an acoustic device configured and operable for remote signal communication with the subject. The acoustic device comprising at least one acoustic transceiver unit configured for transmitting acoustic signals towards the subject and receiving reflected acoustic signals from the subject, and generating data indicative of detection of the received signals.

The system further comprising a control system including: (i) an analyzer module being in data communication with the acoustic device for receiving and analyzing the data indicative of the detected acoustic signals to determine a variation profile data indicative of a relation between the detected signal and the transmitted signal; and (ii) an extractor module configured and operable to extract data indicative of the vital signs profile of the subject from said variation profile data.

Yet another aspect of this disclosure concerns a sensor device for use in monitoring vital signs profile of a subject, the device comprising: an acoustic device configured and operable for remote signal communication with the subject. The acoustic device comprising at least one acoustic transceiver unit configured for transmitting acoustic signals in a frequency range between 30 KHz and 5 MHz towards the subject and receiving reflected acoustic signals, and generating measured data indicative of detection of the received signals. The sensor further comprising a communication utility configured for data communication with a control system via a communication network, to transmit the control system data indicative of the transmitted acoustic signals and the measured data indicative of the detection of the received signals, and receive from the control system analyzed data indicative of the vital signs profile of the subject. The data may comprise a profile of the physical movement of the heart due to heartbeat and respiration. It is to be noted that since the frequencies of heartbeat and respiration differ from each other, the generated profiles, e.g. the graphs, of each of this parameter may be generated independently to the other. Thus, two independent movement profiles may be generated, one due to heartbeat and the other due to respiration.

The analyzed data received from the control system may be indicative of at least one of heart rate, heart rate variability, respiration rate and blood pressure. Furthermore, the system may identify in the analyzed data patterns that are correlated with certain pathologies and provide an alert output indicating the finding of the pathology.

The data indicative of the vital signs profile of the subject received from the control system comprises variation profile data indicative of a relation between the detected signal and the transmitted signal, the device further comprising a control unit configured and operable to extract, from said variation profile data, signals indicative of the vital signs profile of the subject comprising at least one of heart rate, heart rate variability, and respiration.

In some embodiments, the system may be in communication with or include an RF unit that is configured for transmitting RF signals, namely electromagnetic signals within the radio frequency spectrum, towards the subject and detect reflections therefrom. The RF unit is configured to generate RF measured data based on the detected reflections. This data includes the profile of the detected RF signals overtime than includes reflections of the transmitted signals that are transmitted towards the subject. In some specific examples, the RF unit may be configured to transmit the RF signals towards the area of the chest of the subject to obtain reflections that are indicative of BCG of the subject. The analyzer of the system is configured to analyze the RF measured data and determine an RF variation profile data indicative of a relation between the transmitted RF signal and the reflection thereof from the subject. This variation profile results due to a movement of the subject or a part of the subject, such as the chest, during the interaction of the RF signal therewith. The extractor module is configured and operable to extract data indicative of the vital signs profile of the subject based on the acoustic variation profile data and the RF variation profile data. Namely, the extractor may use the combination of the acoustic variation profile data and the RF variation profile data to determine the vital signs of the subject.

In some embodiments, the system may be in communication with or include a sound detector configured to detect sounds produced by the subject and/or the surrounding thereof, and to generate sound data based thereon. The control system further includes a sound analysis module configured to analyze said sound data and determine vital-signs-sound-based-data. The extractor is configured to extract the data indicative of the vital signs profile based on the acoustic variation profile data and the vital-signs-sound-based-data. Namely, the extractor may use the combination of the acoustic variation profile data and the vital-signs-sound-based-data to determine the vital signs of the subject.

In some embodiments, the sound analysis module is configured to perform speech recognition algorithm on the sound data to determine data pieces indicative of the speech of the subject. For example, the sound analysis module may be configured to analyze the sound data to determine the general state of the subject, e.g. whether the subject experience any physical condition that is manifested in its voice.

Either of the monitoring system or the sensor device of this disclosure can be comprised in a personal communication device. For example, the monitoring system and/or the sensor device can be associated with or comprised in a phone device, watches, user dedicated monitor or a vehicle computer.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4A exemplifies a configuration of the noise cancellation module that uses multiple transmitters; FIG. 4B exemplifies a configuration of the noise cancellation module that uses analogic signal; FIG. 4C exemplifies a configuration of the noise cancellation module that uses wideband signal transmission; and FIG. 4D exemplifies a configuration of the noise cancellation module that uses multiple receivers.

EMBODIMENTS

Figure 1A:
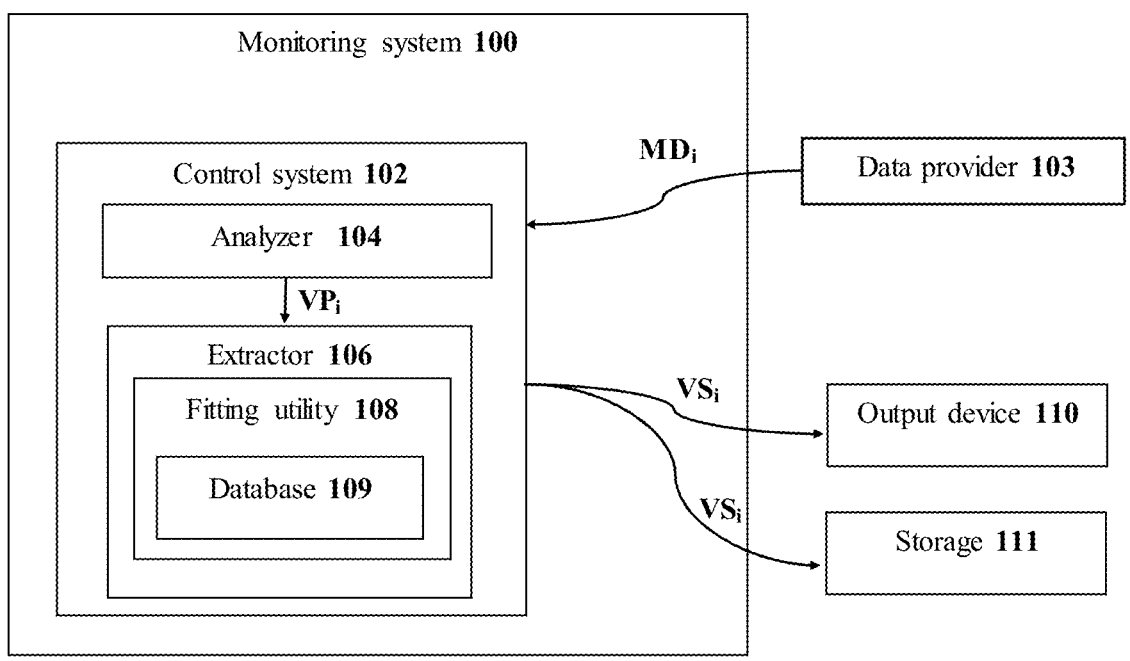
FIGS. 1A-1B are block diagrams of examples of the monitoring system of the present disclosure.

The following are optional embodiments and combinations thereof in accordance with aspects of the present disclosure:

1. A monitoring system for use in determining vital signs profile of a subject, the monitoring system comprising a control system configured for data communication with an acoustic device to receive measured data indicative of reflection of predetermined acoustic signals from the subject, the control system comprising: an analyzer module configured and operable to analyze said measured data and determine a variation profile data indicative of a relation between the predetermined acoustic signal and the reflection thereof from the subject; and an extractor module configured and operable to extract data indicative of the vital signs profile of the subject from said variation profile data.

2. The monitoring system of embodiment 1, further comprising an acoustic device configured and operable for remote signal communication with the subject and obtain said measured data, the acoustic device comprising at least one acoustic transceiver unit configured for transmitting acoustic signals towards the subject and receiving reflected acoustic signals from the subject, and generating the measured data indicative of detection of the received signals.

3. The monitoring system of embodiment 1 or 2, wherein the extractor module comprises a fitting utility for determining at least one vital sign of the subject that satisfies a correlation condition with said variation profile data.

4. The monitoring system of embodiment 3, wherein the fitting utility is configured to determine the at least one vital sign from a plurality of vital signs stored in a database.

5. The monitoring system of embodiment 4, wherein the vital signs stored in the database comprises at least one of the following types of vital signs: theoretical vital signs described by one or more models, and predetermined measured plurality of vital signs.

6. The system of any one of the preceding embodiments, wherein the measured data comprises multiple measured signals, each being indicative of a variation profile data with respect to a reflection of a corresponding acoustic signal of predetermined characteristics.

7. The system of any one of the preceding embodiments, wherein the variation profile data comprises data indicative of general subject's movement, and data indicative of local movement associated with a ballistocardiography (BCG) signature of the subject, the extractor module being configured and operable to process the variation profile data to extract therefrom said data indicative of the BCG signature, thereby obtaining the vital signs profile of the subject.

8. The system of embodiment 7, wherein the extractor module is configured and operable to process the variation profile data to identify shift data indicative of shift in at least one of local frequency and phase in the variation profile from at least one of frequency and phase of the predetermined acoustic radiation/signal.

9. The monitoring system of embodiment 8, wherein the extractor module is configured and operable to process the variation profile data by applying to said data one or more wavelet transform models, Fourier analysis based frequency estimation models, Machine Learning models or any combination thereof.

10. The system of any one of the preceding embodiments, further comprising a noise reduction system configured and operable to suppress signal components propagating towards the acoustic device and being associated with acoustic signals coming from outside a region of interest in the subject, thereby enabling to extract the reflections of the predetermined acoustic radiation/signal from the region of interest.

11. The system of embodiment 10, wherein the control system comprises a noise reduction module of said noise reduction system, the noise reduction module being configured and operable to process the received signals, to suppress signal components associated with acoustic signals received from outside a region of interest in the subject.

12. The system of embodiment 11, wherein the noise reduction module is adapted to identify the acoustic signals from the outside of the region of interest as signals having the predetermined characteristics different from signals coming from the region of interest.

13. The system of embodiment 12, wherein the noise reduction module is adapted to identify the acoustic signals from the outside of the region of interest as having the predetermined characteristics corresponding to reflections of acoustic radiation/signal from substantially static objects.

14. The system of any one of embodiments 10 to 13, wherein the acoustic device comprises a noise reduction device of said noise reduction system, the noise reduction device being configured and operable to operate said at least one acoustic transceiver unit to transmit acoustic signals comprising signal components having characteristics oppositely matching characteristics of acoustic signals propagating towards the acoustic device from outside the region of interest.

15. The system of embodiment 14, wherein the acoustic device comprising a control unit comprising a signal generator operating the acoustic transceiver unit, which comprises a main transceiver and a secondary transceiver, the control unit being configured and operable to process preliminary measured data obtained by the acoustic transceiver unit to identify acoustic signal components from the outside of the region of interest as signals having predetermined characteristics corresponding to reflections of acoustic radiation/signal from substantially static objects, and operating the signal generator to operate the secondary transceiver to transmit acoustic signals having characteristics oppositely matching said predetermined characteristics thereby preventing reflections of acoustic radiation/signal from substantially static objects to be received.

16. The system of embodiment 13, wherein the acoustic device comprises multiple receivers arranged at predetermined locations with respect to said at least one acoustic transceiver unit, the noise reduction module being configured and operable to analyze a combined output signal of said multiple receivers to thereby identify the acoustic signals from the outside of the region of interest.

17. The system of any one of embodiments 10 to 16, wherein the noise reduction system comprises a cancellation module configured and operable to utilize input data indicative of characteristics of the predetermined acoustic signals and process data indicative of acoustic signals being received by applying thereto data corresponding to acoustic signals oppositely matching the characteristics of the predetermined acoustic signals.

18. The system of embodiment 17, wherein said cancellation module has one of the following configurations: (i) is configured as an analog circuit for applying said processing to the acoustic signals being received by the transceiver unit; and (ii) is configured as a digital processor for applying said processing to digital representation of the received acoustic signals.

19. The system of embodiment 1, wherein the control system comprises a noise reduction system comprising a cancellation module configured and operable to utilize input data indicative of characteristics of the predetermined acoustic signals and process data indicative of acoustic signals being received by applying thereto data corresponding to acoustic signals oppositely matching the characteristics of the predetermined acoustic signals.

20. The system of any one of embodiments 10 to 19, wherein the extracted reflections of the predetermined acoustic signals from the region of interest are signals shifted from the predetermined acoustic signals in at least one of frequency and phase parameters.

21. The system of any one of the preceding embodiments, wherein the analyzer module is in data communication with a motion sensor device, which is configured and operable for sensing a movement profile of the subject and generating corresponding motion data.

22. The system of any one of the preceding embodiments, wherein the analyzer module is in data communication with an image acquisition device, which is configured and operable for visually monitoring a movement of the subject and generating image data indicative thereof.

23. The system of any one of embodiments 2 to 22, wherein the acoustic device is configured and operable in a frequency range between 30 KHz and 5 MHz.

24. The system of any one of the preceding embodiments, wherein the variation profile data is indicative of a ballistocardiograph (BCG) signal or chest movement profile due to respiration.

25. The system of any one of the preceding embodiments, wherein the vital sign to be determined is indicative of at least one of heart rate, heart rate variability, respiration rate and blood pressure.

26. The system of any one of the preceding embodiments, wherein the control system is configured for communication with an RF unit to receive RF measured data based indicative of reflections of RF signals from the subject; the analyzer is configured to analyze said RF measured data and determine an RF variation profile data indicative of a relation between the transmitted RF signal and the reflection thereof from the subject; and the extractor module is configured and operable to extract data indicative of the vital signs profile of the subject based on the acoustic variation profile data and the RF variation profile data.

27. The system of embodiment 26, further comprising said RF unit, the RF unit is configured for transmitting RF signals towards the subject and detect reflections therefrom and generate said RF measured data based on the detected reflections.

28. The system of any one of the preceding embodiments, wherein the control unit is configured for communication with a sound detector for receiving sound data indicative of sounds produced by the subject and the surrounding thereof; the control system comprising a sound analysis module configured to analyze said sound data and determine vital-signs-sound-based-data, the extractor is configured to extract the data indicative of the vital signs profile based on the acoustic variation profile data and the vital-signs-sound-based-data.

29. The system of embodiment 28, further comprising a sound detector configured to detect sounds produced by the subject and the surrounding thereof to generate said sound data based thereon.

30. The system of embodiment 28 or 29, wherein the sound analysis module is configured to perform speech recognition algorithm on the sound data to determine data pieces indicative of the speech of the subject.

31. A system for determining vital signs profile of a subject comprising:
an acoustic device configured and operable for remote signal communication with the subject, the acoustic device comprising at least one acoustic transceiver unit configured for transmitting acoustic signals towards the subject and receiving reflected acoustic signals from the subject, and generating data indicative of detection of the received signals;
a monitoring system that comprises a control system comprising:
an analyzer module being in data communication with the acoustic device for receiving and analyzing the data indicative of the detected acoustic signals to determine a variation profile data indicative of a relation between the detected signal and the transmitted signal;
an extractor module configured and operable to extract data indicative of the vital signs profile of the subject from said variation profile data.

32. The monitoring system of any one of embodiments 1-31, wherein said variation profile comprises phase variation over time of the reflection of predetermined acoustic signals from the subject.

33. The monitoring system of any one of embodiments 1-32, wherein said measured data comprises a first signal component indicative of movement associated with the BCG movements of the subject and a second signal component indicative of either body movements of the subject not associated with BCG movements or static reflections,
the monitoring system further comprising a noise cancelling unit configured for: (i) determining a time window of said reflection of predetermined acoustic signals in correlation with the reference signal to define a time-windowed signal, (ii) applying a cancelation function between the time-windowed signal and the reference signal to determine a noise-residue signal, (iii) applying a tuning function between the noise-residue signal and the second signal component to determine a noise cancellation signal, and (iv) applying the noise cancellation signal on the first signal component to determine a noise-free signal;
wherein the analyzer module is configured and operable to analyze said noise-free signal and determine said variation profile.

34. The system of embodiment 33, wherein the monitoring system is as defined in any one of embodiments 1-32.

35. A sensor device for use in monitoring vital signs profile of a subject, the device comprising:
an acoustic device configured and operable for remote signal communication with the subject, the acoustic device comprising at least one acoustic transceiver unit configured for transmitting acoustic signals in a frequency range between 30 KHz and 5 MHz towards the subject and receiving reflected acoustic signals, and generating measured data indicative of detection of the received signals;

a communication utility configured for data communication with a control system via a communication network, to transmit to the control system data indicative of the transmitted acoustic signals and the measured data indicative of the detection of the received signals, and receive from the control system data indicative of the vital signs profile of the subject.
36. The sensor device of embodiment 35, wherein the data indicative of the vital signs profile of the subject received from the control system comprises the vital sign indicative of at least one of heart rate, heart rate variability, respiration rate and blood pressure.
37. The sensor device of embodiment 36, wherein the data indicative of the vital signs profile of the subject received from the control system comprises variation profile data indicative of a relation between the detected signal and the transmitted signal, the device further comprising a control unit configured and operable to extract, from said variation profile data, signals indicative of the vital signs profile of the subject comprising at least one of heart rate, heart rate variability, respiration rate and blood pressure.
38. A personal communication device comprising the monitoring system of any one of embodiments 1 to 32.
39. A personal communication device comprising the sensor device of any one of embodiments 35 to 37.
40. The personal communication device of embodiment 38 or 39, configured as one of the following: a phone device, watches, user dedicated monitor, a vehicle computer, data storage and computing device.
41. The monitoring system or the sensor device of any one of embodiments 1-32 or 35-37 configured to be installed in a vehicle for monitoring at least one individual within the vehicle.
42. The monitoring system or the sensor device of any one of embodiments 1-32 or 35-37 configured to be fixedly associated with a crib for monitoring an infant within the crib.

DETAILED DESCRIPTION OF EMBODIMENTS

The present invention concerns a monitoring system for determining vital signs of a subject. The vital signs are being determined by analyzing a variation profile, typically a shift in frequency or phase, of a reflected acoustic signal (e.g. ultrasonic signal) that is transmitted from a remote location of the subject. In other words, the acoustic signal is transmitted from an acoustic device towards the subject, propagates through the medium between the device and the subject (e.g. air, or other mediums that separate between the monitoring system to the subject), being reflected by the subject and the reflected signal propagates back to the acoustic device and is analyzed to determine the vital signs.

Figure 1B:
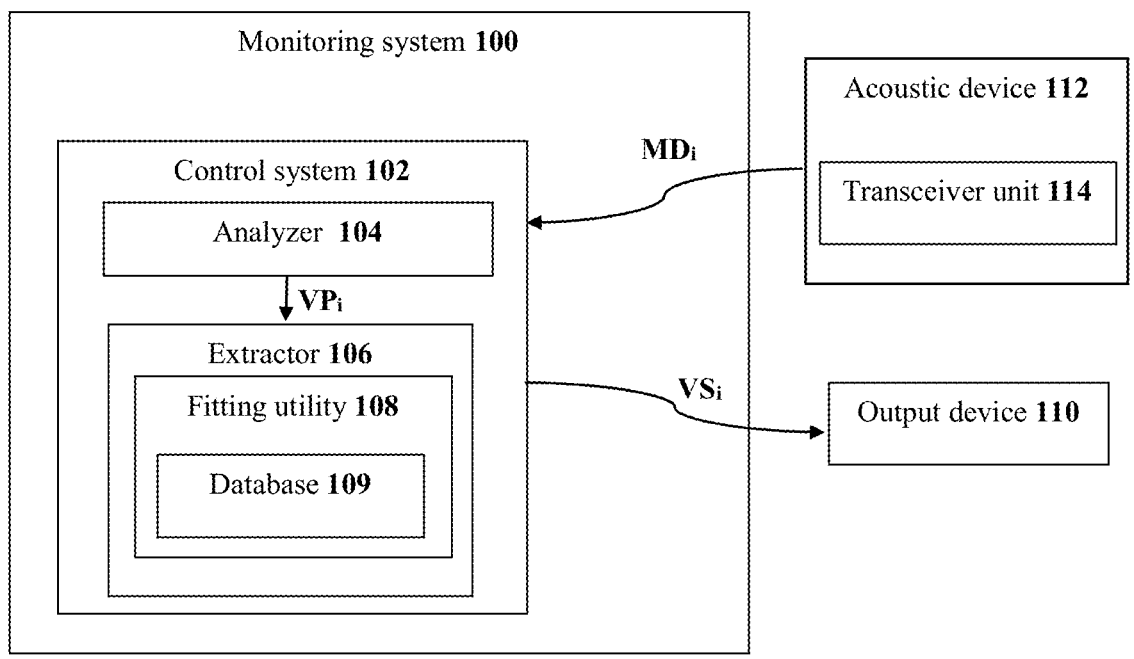

Reference is first made to FIG. 1A-1B which are block diagrams showing schematic examples of embodiments of the monitoring system of the present invention. In FIG. 1A, the monitoring system 100 comprising a control system 102 that is in data communication with a data provider 103 for receiving measured data MD; of an acoustic signal. The data provider 103 stores and communicates the measured data MD; which includes data of the transmitted signal and the received signal. The received signal may be shifted in phase and frequency from the transmitted signal due to the response of the signal with the subject, e.g. reflection from the subject's body, or even more particularly, the subject's chest. The data provider 103 may be a storage device that is in data communication with a measurement device, such as an acoustic device, or can be the measurement device itself that is in online data communication with the control system 102.

The control system 102 comprising an analyzer 104 that receives and analyzes the measured data MD; to identify and determine a variation profile data $VP_i$ indicative of a relation between the predetermined transmitted acoustic signal and the reflection thereof from the subject. The variation profile $VP_i$ is indicative of the vital signs profile of the subject and an extractor 106, that is in data communication with the analyzer 104, is configured to extract the vital signs from the variation profile $VP_i$. It is to be noted that the extractor 106 can be a part of the control system 102 or can be in the form of a remote unit external to the control unit 102. In some embodiments, the extractor 106 can be external to the monitoring system 100.

The extractor 106 may comprise a fitting utility 108 configured to identify a predetermined variation profile that is stored in a database 109 and that matches the obtained variation profile $VP_i$, to determine at least one vital signs $VS_i$. In other words, the fitting utility 108 stores a plurality of variation profiles, each is correlated with a specific vital sign or indicative thereof, and when a measured variation profile $VP_i$ is obtained, the fitting utility 108 correlates between the measured variation profile $VP_i$ and the stored variation profile from the database 109, that satisfies a correlation condition therewith.

The variation profile $VP_i$ may be determined by applying transformation models to the obtained measured data $MD_i$ such as, but not limited to, wavelet transform models.

Figure 5:
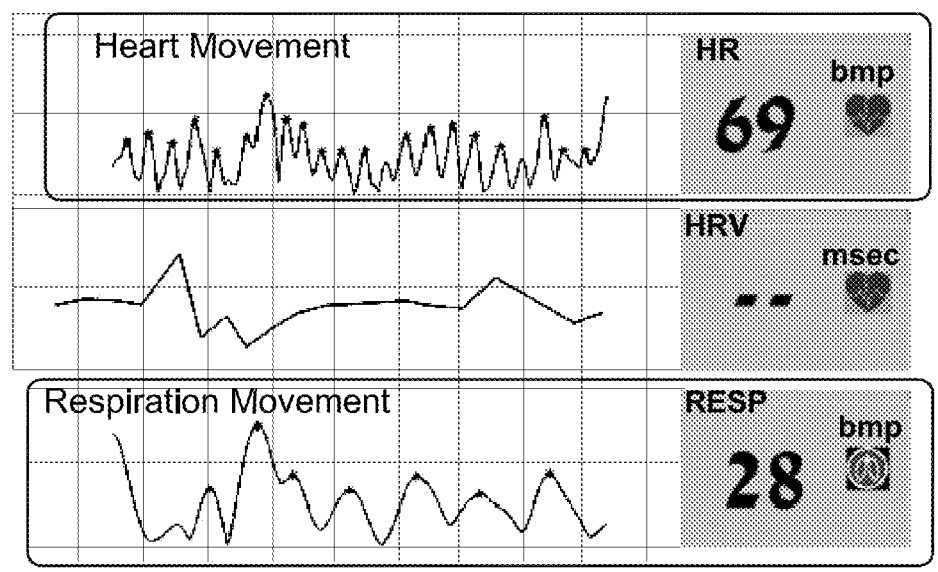
FIG. 5 is a schematic illustration of an example of a presentation of the vital signs graphs and measures extracted by the system of the present disclosure.

An output device 110 in data communication with the control system 102, receives the data indicative of the vital sign $VS_i$ and may present it either in vocal or visual presentation (e.g. by speakers or monitors). Otherwise, the data can be stored in a storage device 111 for farther uses, for example for healthcare monitoring. Example for a visual presentation of the vital signs is illustrated in FIG. 5. Heart rate, heart rate variability and respiration graphs are presented on the left-hand side from top to bottom, and on the right-hand side, the analyzed values are presented respectively.

FIG. 1B differs from FIG. 1A by that the measured data MD; is received from an acoustic device 112 having a transceiver unit 114 and is in data communication with the monitoring system 100, and specifically with the control system 102. The transceiver unit 114 transmitting acoustic signals towards the subject, such that there is no contact between the transceiver unit 114 and the subject, namely a remote signal communication. The reflected signals from the subject, and maybe other reflected signals, are being received in the transceiver unit 114. This measured data MD; is communicated to the control system 102, typically by an online, real-time communication.

In this manner, that the signal communication between the transceiver unit 114 and the subject is contact-free, the variation profile $VP_i$ of the acoustic signals, namely the shift in phase and frequency of the reflected signals from the transmitted signals, is indicative of the movement of the subject. As will be also explained below, a data indicative of local movements, such as chest movements of the subject due to heartbeat and respiration, can be identified from the data indicative of the movement of the subject. For example, the identified data can be such that is associated with a ballistocardiography (BCG) signature of the subject.

In different figures throughout the application, like elements were given like numerical references shifted by 100, 200, 300 etc., namely meaning they serve a similar function in the invention. For example, the transceiver unit 114 in FIG. 1 serves the same purpose as the transceiver unit 214 in FIG. 2.

Figure 2A:
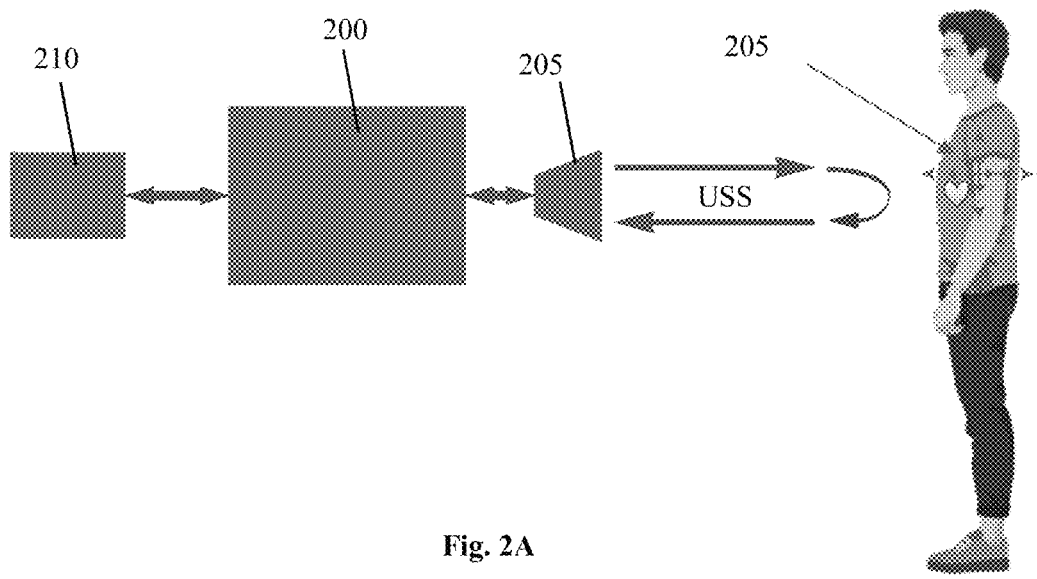
FIG. 2A-2B are schematic illustrations of examples of two embodiments of the monitoring system of the present disclosure.
Figure 2B:
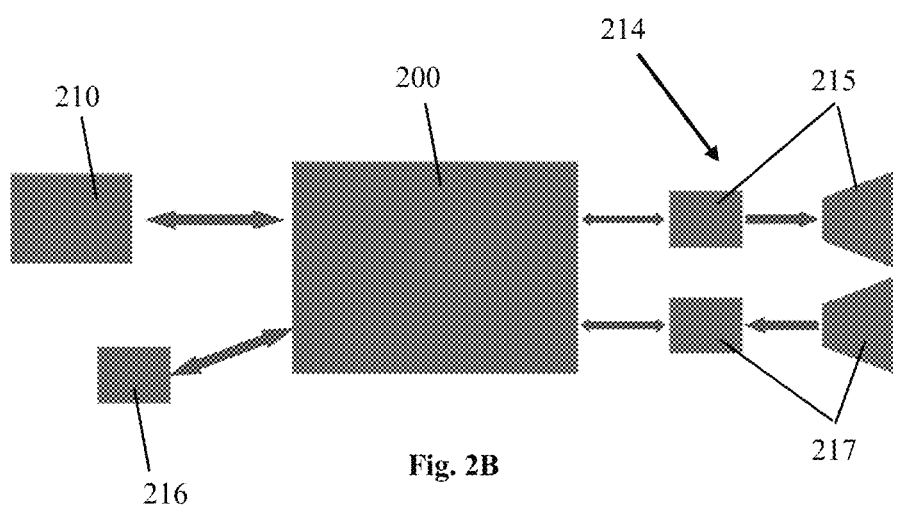

Schematic illustrations of examples of the basic operation of the system are shown in FIGS. 2A and 2B. In FIG. 2A the monitoring system 200 comprising an ultrasound transceiver 214 that is configured to transmit and receive ultrasonic signals USS. The ultrasonic signals are transmitted toward and reflected from the subject 205. The reflected signals are being shifted in time/phase and frequency due to, among others factors, movement of the chest. The received signals are communicated to the monitoring system 200 for determining therefrom data indicative of the vital signs of the subject 205, such as heart rate, heart rate variability, respiration rate and blood pressure. The data of the vital signs is then communicated to a monitor 210 to be presented visually.

Another mode of operation is shown in FIG. 2B in which the transceiver unit 214 comprises separate components for transmitting and receiving acoustic signals, namely a transducer 215 that transmits the acoustic signals and receiver 217 that receives and detects the acoustic signals. Furthermore, external sensory system(s) 216 may be in data communication with the monitoring system 200 and the data therefrom is processed together with the measured data $MD_i$ to determine the vital signs of the subject. Examples of sensory systems are motion sensors (e.g. accelerometer, gyroscope) and visual imaging systems such as a camera.

During the operation of the system, signals reflected from objects that are outside of the region of interest, i.e. the subject, may be received in the acoustic device and are considered as noise.

Figure 3:
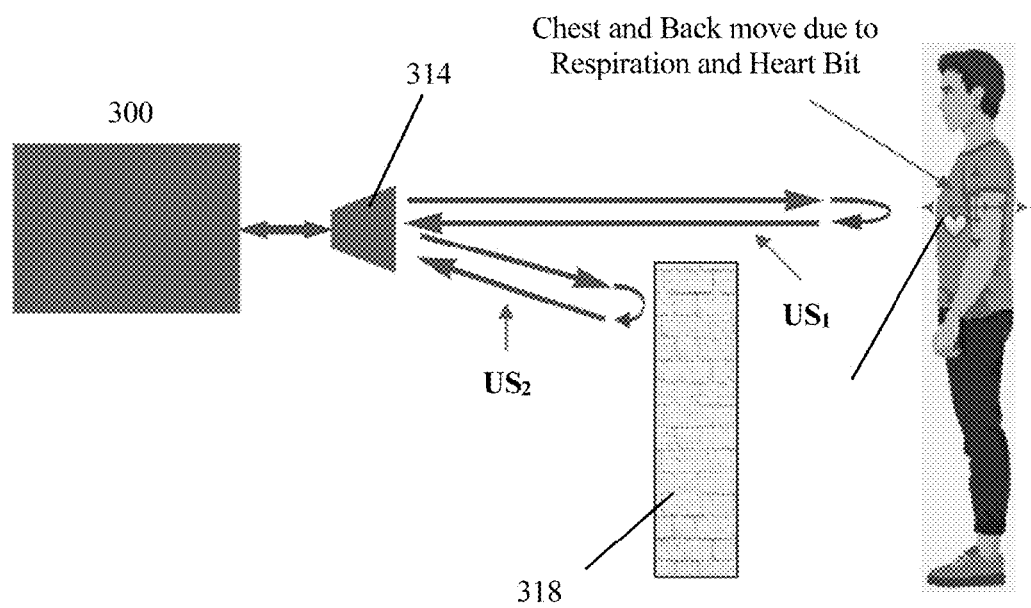
FIG. 3 is a schematic illustration exemplifying the basic operation of the monitoring system of the present disclosure in the presence of a subject and a static object.

FIG. 3 is a schematic illustration exemplifying noise signals received in the transceiver unit 314 of the monitoring system 300 resulted from reflection from static objects. As can be appreciated, some of the ultrasonic signals $US_1$ transmitted by the transceiver unit 314 are reflecting from the subject's chest and propagating back to and received by the transceiver unit 314 while some other part of the ultrasonic signals $US_2$ is reflecting from a static object 318 and propagating back to and received by the transceiver unit 314 and is considered as noise. Reduction of such noise may improve the accuracy of the system due to increase in the signal to noise ratio.

FIGS. 4A-4D are schematic illustrations of examples of noise reduction systems of the monitoring system of the present invention.

Figure 4A:
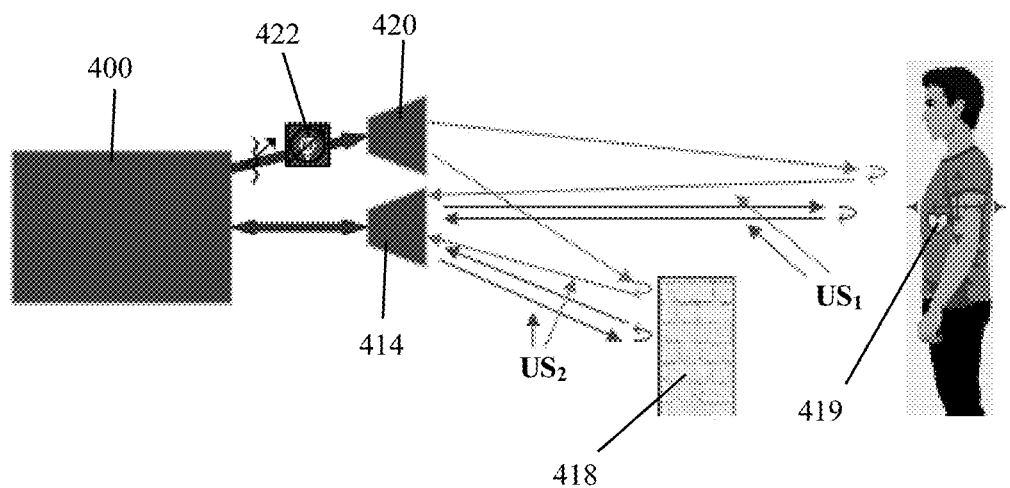
FIGS. 4A-4D are schematic illustrations for various embodiments of the noise cancellation module.

First, reference is being made to FIG. 4A in which the monitoring system 400 comprising a transceiver unit 414 configured for transmitting and receiving acoustic signals. As can be appreciated, some of the transmitted signals are reflected from the subject $US_1$ and carry data indicative of movement thereof, while some other portion of the acoustic signal $US_2$ is reflected from a static object 418 which is noise. The noise signal is identified by the monitoring system 400 due to its constant and continuous signal form and the monitoring system 400 communicates the data indicative of noise signals, in particular static noise, to an additional transducer unit 420 that comprises a signal generator unit 422 in order to generate and transmit an additional acoustic signal such that its reflection from the static object(s) 418, when received by the transceiver unit 414, will have characteristics that will suppress the noise signals. In other words, the transducer unit 420 is configured to generate and transmit noise cancelling signals to be received by the transceiver unit 414, directly or by reflecting from the static object(s) such that the eventual measured signal will derive substantially from the region of interest, namely the subject and preferably the subject's chest. It should be noted that the data indicative of noise signals may comprise also data indicative of the relative position of the static object 418 to either the transceiver unit 414, the transducer unit 420 or any combination thereof.

Figure 4B:
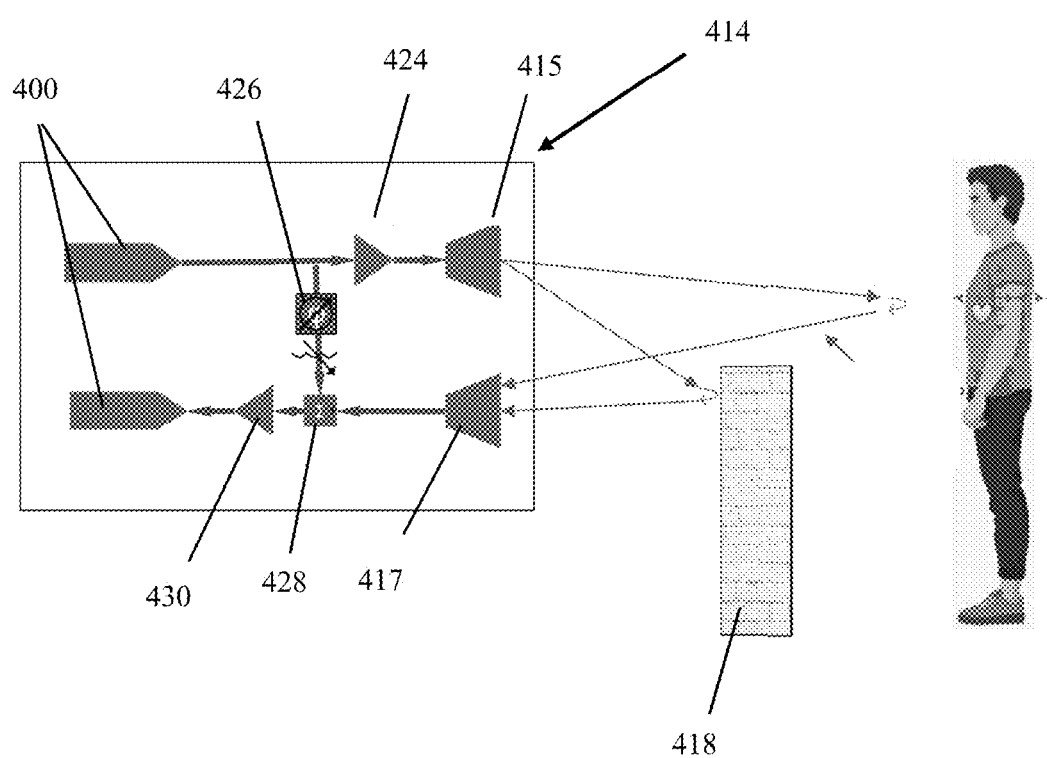

Referring to FIG. 4B, the monitoring system 400 comprising a transceiver unit 414 that has separated components for transmitting and receiving acoustic signals, namely a transducer 415 and a receiver 417 and a signal amplifier 424 to generate an amplified signal to be transmitted by the transducer 415. Similar to the example above, the transducer 415 transmit acoustic signals and some of the signal $US_1$ is reflected from the subject and some of the acoustic signal $US_2$ is reflected from the static object 418. Therefore, the signal is received in the receiver 417 includes the reflections from the subject and from the static object 418 which are constant and continuous noise. This noise is identified and monitored by the monitoring system 400 so during operation, the monitoring system 400 instructs an analog signal generator 426 to generate a signal with suitable characterization to suppress the noise signal, the analog signal is directly communicated to the receiver's input unit 428 such that the superposition of the received signal noise and the analog signal will be generally null, namely the noise signal will be canceled. The clean signal carrying substantially only data indicative of the movement of the subject will be amplified by a receiver's amplifier 430 and will be communicated to the monitoring system 400 for further processing as explained above. It should be understood that the analog signal generator 426 can be replaced by a digital signal generator which functions for a similar purpose only that the cancelling signal is only generated in the digital domain and the noise is cancelled digitally in the processing process.

Figure 4C:
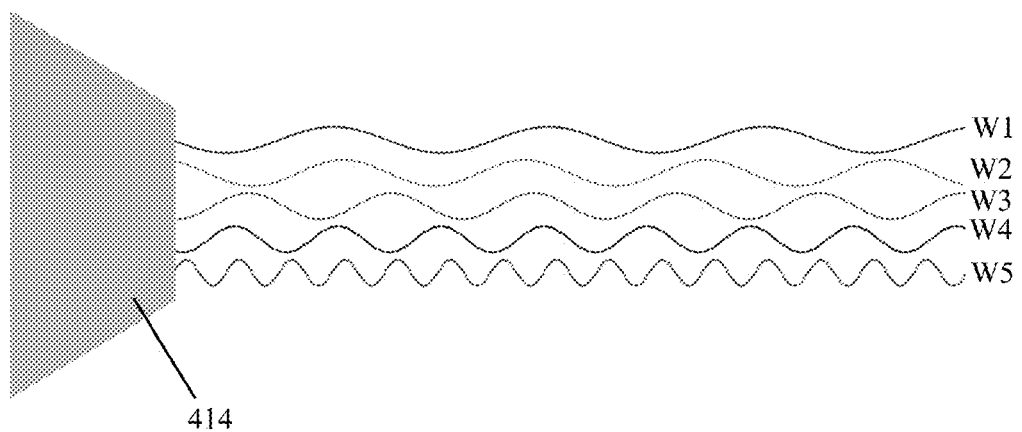

Another example to overcome noise or echo signals is by using a wideband signal transmission as exemplified in FIG. 4C. The figure shows an example of the reflections from a static object of various waves signals with different wavelengths that are transmitted by the transceiver unit 414. As can be appreciated the upper two waves W1 and W2 are received in the transceiver unit 414 with a relatively high amplitude while the lower three waves W3, W4 and W5 are received in a point where their amplitude is relatively low. The monitoring system 400 (not shown) is configured and operable to identify the amplitude or the intensity of each wave signal and adjust its amplification such that the incoming signal from the various wave signals will be substantially equal. In our example of FIG. 4C, the amplification/gain of waves W1 and W2 will be decreased while the amplification/gain of waves W3, W4 and W5 will be increased.

Figure 4D:
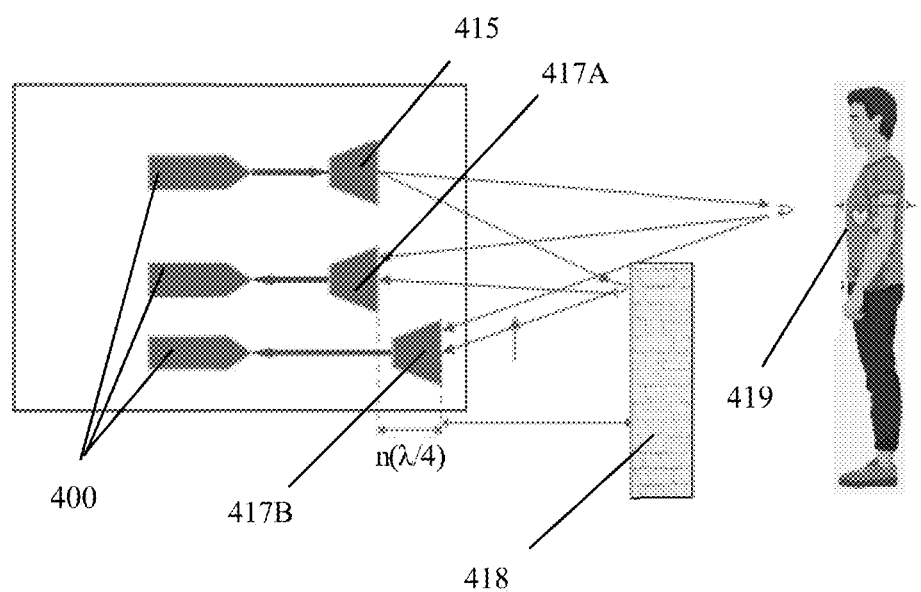

FIG. 4D exemplifies another configuration of the system for dealing with noise signals by using multiple receivers. The system 400 comprises a transducer 415 that transmits acoustic signals. The signals are reflected from the subject 419, which constitutes the region of interest, and from static object 418. A first receiver 417A to disposed at a first position and a second receiver 417B disposed at a second position. In this non-limiting example, both of the receivers receive signals from the subject 419 and the static object 418. The receivers 417A, 417B are set in a predetermined position with respect to one another such that the received signals may be received in each of the receivers with a different phase, namely the amplitude of the received signals differ between the first 417A and the second receiver 417B. For example, the second receiver may be disposed at a position that is a multiple of an integer of a quarter of the wavelength n($\lambda$/4). In this specific example, if one of the receivers receives signal with a maximum amplitude, the other receives the same signal with a minimum amplitude. When a signal is received from a static object, it is discernable from other signals that derive from moving objects, namely the subject or more specifically the chest of the subject. For example, the signal from the static objects may be a continuous standing wave. The amplification of the received signals in each of the receivers can be configured according to the intensity of noise received in each of the receiver. For example, if the first receiver 417A receives the noise signal from the static object 418 of about its maximum intensity, the amplification thereof may be reduced with respect to the second receiver 417B that receives the noise signal of about its minimum intensity. In this manner the received signal to noise may be increased. Furthermore, the location of the static object may be determined by the combination of the received signals.

It is to be noted that any of the configurations of the noise cancellation module exemplified above, may be implemented in the system of the present disclosure alone or in any combination with the other configurations.

Figure 6:
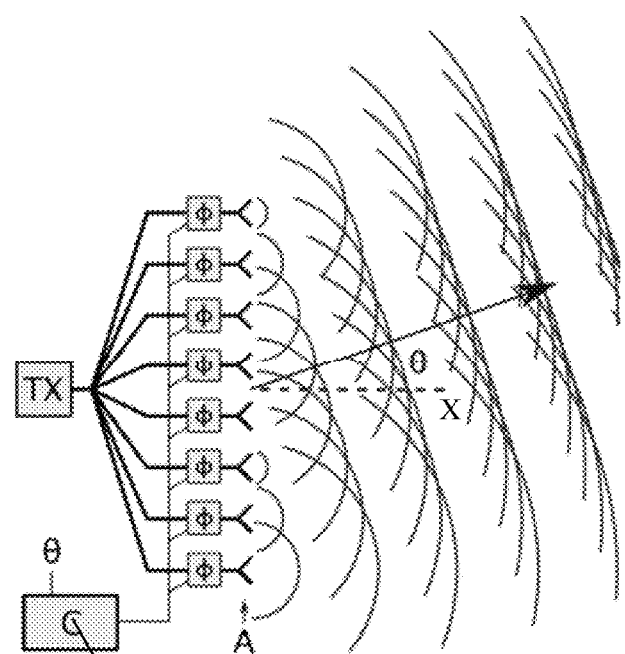
FIG. 6 is a schematic illustration of an example of a phased array structure of the system of the present disclosure formed of various acoustic transducers synchronized with their phase shift.

The use of multiple acoustic transducers and/or receivers may provide additional advantages. For example, as illustrated in FIG. 6, multiple transducers may be used as a phased array for electrically stirring the acoustic signal. As exemplified in FIG. 6 the transducers may transmit signals with synchronized phase shift so the generated acoustic signal is diverted from the main axis X by an angle $\theta$. The synchronization of the signals is done by a synchronizing unit 734.

Figure 7:
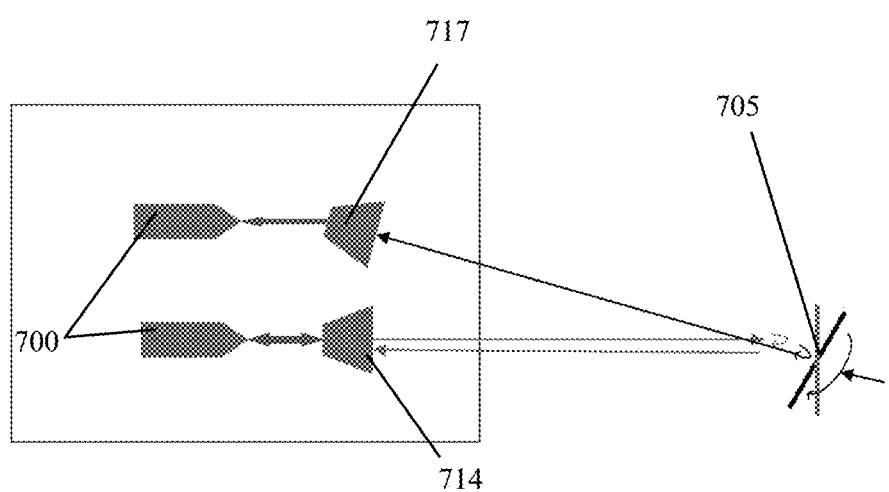
FIG. 7 is a schematic illustration of an embodiment of the system of the present invention exemplifying the use of multiple receivers to increase coverage of the system.

FIG. 7 is a schematic illustration of an embodiment of the monitoring system of the present invention. The monitoring system includes multiple receivers disposed in different distance and angles with respect to the region of interest. In this example, the monitoring system 700 comprises a transceiver unit 714 configured to transmit and receive acoustic signals and an additional receiver 717 that its main axis is tilted/angled with respect to the transceiver unit 714. Signals that are reflected from the region of interest 705 in a deflection that cannot be received, or received with low intensity in the first transceiver unit 714, may be received in the additional receiver 717. In this manner, the receiving coverage is increased and the loss of data due to movements, rolls, yaws, tilts etc., of the region of interest, is reduced. It is to be noted that to obtain a similar effect, the monitoring system can comprise multiple transducers that transmit acoustic signal from multiple directions towards the region of interest.

Figure 8:
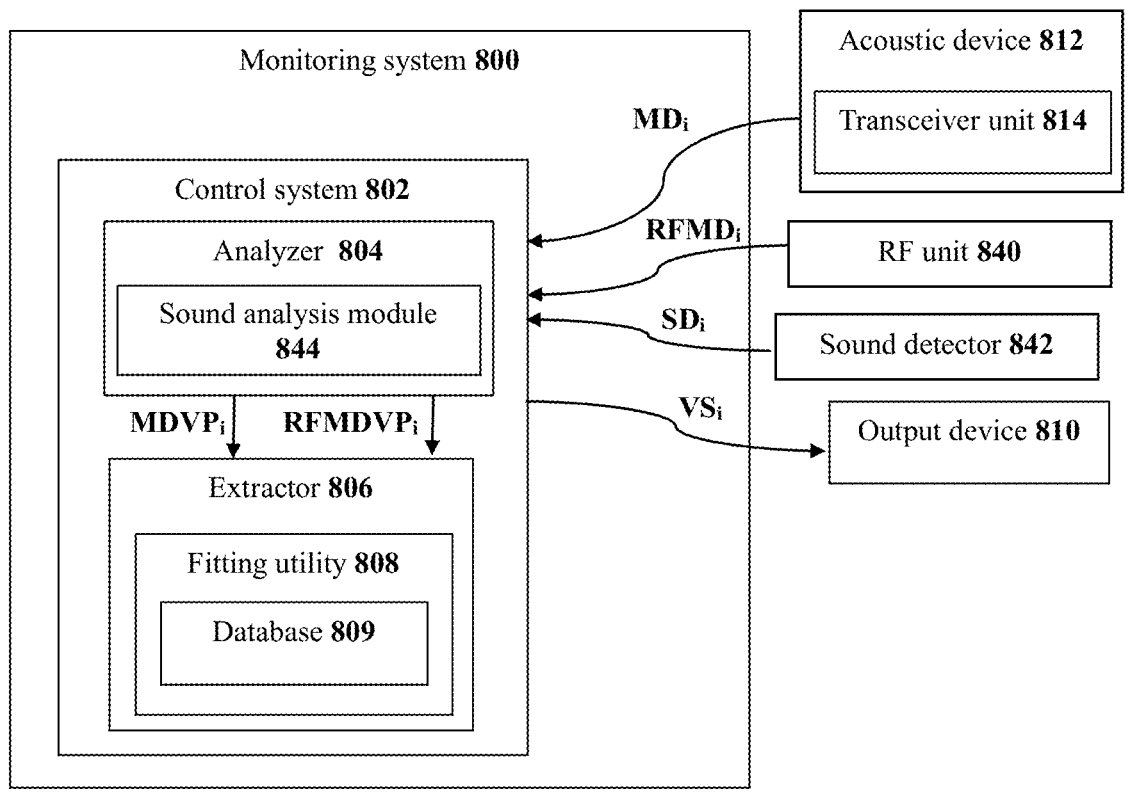
FIG. 8 is a block diagram of a non-limiting example of an embodiment of the monitoring device according to the present disclosure.

FIG. 8 is a block diagram of a non-limiting example of an embodiment of the monitoring device according to the present disclosure. The figure differs from FIG. 1B by that it exemplifies additional data providers for the monitoring system 800. In this example, the monitoring system 800 is in data communication with an RF unit 840 that is configured to generate and transmit to the monitoring system 800 RF measured data $RFMD_i$ that is indicative of reflections of RF signals from the subject or parts thereof. The monitoring system 800 is further in communication with a sound detector 842 that is configured to transmit to the monitoring system 800 sound data $SD_i$ indicative of sounds originated from the subject or its surrounding. The control system 802 receives the RF measured data $RFMD_i$ and the sound data $SD_i$, analyze it and determine the vital signs $VS_i$ of the subject based on the combination of the acoustic measured data $MD_i$, the RF measured data $RFMD_i$ and the sound data $SD_i$. It is to be noted that the analyzer 804 generates variation profile for the RF measured data $RFMD_i$ and the acoustic measured data $MD_i$ independently, namely an RF measured data variation profile $RFMDVP_i$ and an acoustic measured data variation profile $MDVP_i$, respectively. The analyzer further includes sound analysis module 844 for analyzing the sound data $SD_i$, for example by applying thereon speech recognition techniques.

Figure 9:
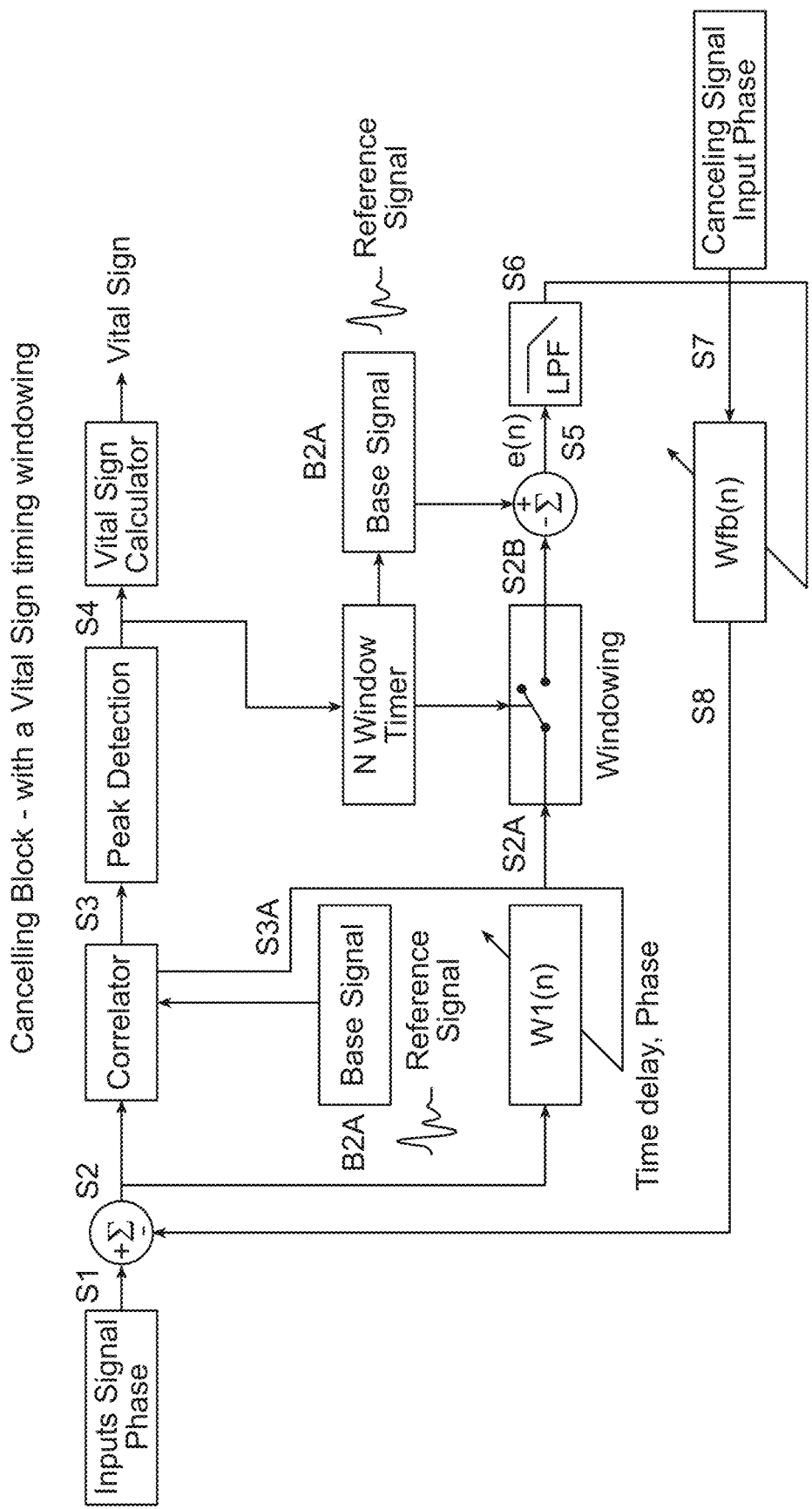
FIG. 9 is a schematic illustration of an embodiment of the monitoring signal, exemplifying a non-limiting example of realization of a cancellation unit/system.

FIG. 9 is a block diagram of an embodiment of the monitoring system that includes a noise cancelling unit. FIG. 9 shows an input signal S1 that is received by a correlator S2, namely a fitting utility, to be correlated or matched with a reference signal that is stored in a memory. Once a correlation condition is being satisfied, the vital sign associated with the reference signal is being recorded by a peak detector S3. The combination of consecutive vital signs records yields a vital sing profile over time S4. To refine the input signal for the correlation with the reference signal, only the time window of the input signal that had the best match with the reference signal is selected and all the samples of the input signal in said time windows are being subtracted from the matching reference signal. The subtraction of these two signals S5 is passed via a low pass filter to obtain a noise-residue signal S6.

The system is configured to receive an input of a cancelling signal that is indicative of either movements of the body that are not associated with the BCG movement or of reflections of static signals. This can be obtained by detecting reflections from two or more receivers, one is placed to obtain the reflections associated with the BCG movements and the other is placed to obtain the reflections associated with the cancelling signal.

The cancelling signal is passed through a tunable filter that is configured to tune the cancelling signal to be in phase and amplitude with the input signal, based on the noise-reside signal that is used in said tunable filter. The noise cancellation signal S8 that is the result of the tunable filter is applied on the input signal S1 in a closed loop control configuration to be able to match a noise-reduced signal with a reference signal to increase the accuracy of the monitoring system.

The invention claimed is:

1. A monitoring system for use in determining vital signs profile of a subject, the monitoring system comprising a control system configured for data communication with an acoustic device to receive measured data indicative of reflection of predetermined acoustic signals from the subject, the control system comprising: an analyzer module configured and operable to analyze said measured data and determine a variation profile data indicative of a relation between the predetermined acoustic signal and the reflection thereof from the subject; and an extractor module configured and operable to extract data to indicative of the vital signs profile of the subject from said variation profile data;

the extractor module comprises a fitting utility for determining at least one vital sign of the subject that satisfies a correlation condition with said variation profile data;

the fitting utility is configured to match between the variation profile obtained from the measured data and a reference signal associated with predetermined theoretical data of vital signs or a predetermined collected data of measurements of a plurality of vital signs;

wherein the variation profile data comprises data indicative of general subject's movement, and data indicative of local movement associated with a ballistocardiography (BCG) signature of the subject, the extractor module being configured and operable to process the variation profile data to extract therefrom said data indicative of the BCG signature, thereby obtaining the vital signs profile of the subject.

2. The monitoring system of claim 1, further comprising an acoustic device configured and operable for remote signal communication with the subject and obtain said measured data, the acoustic device comprising at least one acoustic transceiver unit configured for transmitting acoustic signals towards the subject and receiving reflected acoustic signals from the subject and generating the measured data indicative of detection of the received signals.

3. The monitoring system of claim 1, wherein said variation profile comprises phase variation over time of the reflection of predetermined acoustic signals from the subject.

4. The monitoring system of claim 1, wherein said measured data comprises a first signal component indicative of movement associated with the BCG movements of the subject and a second signal component indicative of either body movements of the subject not associated with BCG movements or static reflections,
the monitoring system further comprising a noise cancelling unit configured for: (i) determining a time window of said reflection of predetermined acoustic signals in correlation with the reference signal to define a time-windowed signal, the time-windowed signal is typically not varying in time and each time-windowed signal is a signal that applies only for a specific correlation time, (ii) applying a cancelation function to between the time-windowed signal and the reference signal to determine a noise-residue signal, (iii) applying a tuning function between the noise-residue signal and the second signal component to determine a noise cancellation signal, and (iv) applying the noise cancellation signal on the first signal component to determine a noise-free signal;
wherein the analyzer module is configured and operable to analyze said noise-free signal and determine said variation profile.

5. The monitoring system of claim 1, wherein the fitting utility is configured to determine the at least one vital sign from a plurality of vital signs stored in a database;
wherein the vital signs stored in the database comprises at least one of the following types of vital signs: theoretical vital signs described by one or more models, and predetermined measured plurality of vital signs.

6. The system of claim 1, wherein the measured data comprises multiple measured signals, each being indicative of a variation profile data with respect to a reflection of a corresponding acoustic signal of predetermined characteristics.

7. The system of claim 1, wherein the extractor module is configured and operable to process the variation profile data to identify shift data indicative of shift in at least one of local frequency and phase in the variation profile from at least one of frequency and phase of the predetermined acoustic signals.

8. The monitoring system of claim 1, wherein the extractor module is configured and operable to process the variation profile data by applying to said data one or more wavelet transform models, Fourier analysis based frequency estimation models, Machine Learning models or any combination thereof.

9. The system of claim 1, further comprising a noise reduction system configured and operable to suppress signal components propagating towards the acoustic device and being associated with acoustic signals coming from outside a region of interest in the subject, thereby enabling to extract the reflections of the predetermined acoustic signals from the region of interest.

10. The system of claim 9, wherein the control system comprises a noise reduction module of said noise reduction system, the noise reduction module being configured and operable to process the received signals, to suppress signal components associated with acoustic signals received from outside a region of interest in the subject;
wherein the noise reduction module is adapted to identify the acoustic signals from the outside of the region of interest as signals having the predetermined characteristics different from signals coming from the region of interest.

11. The system of claim 9, wherein the acoustic device comprises a noise reduction device of said noise reduction system, the noise reduction device being configured and operable to operate said at least one acoustic transceiver unit to transmit acoustic signals comprising signal components having characteristics oppositely matching characteristics of acoustic signals propagating towards the acoustic device from outside the region of interest.

12. The system of claim 11, wherein the acoustic device comprising a control unit comprising a signal generator operating the acoustic transceiver unit, which comprises a main transceiver and a secondary transceiver, the control unit being configured and operable to process preliminary measured data obtained by the acoustic transceiver unit to identify acoustic signal components from the outside of the region of interest as signals having predetermined characteristics corresponding to reflections of acoustic signals from substantially static objects, and operating the signal generator to operate the secondary transceiver to transmit acoustic signals having characteristics oppositely matching said predetermined characteristics thereby preventing reflections of acoustic signals from substantially static objects to be received.

13. The system of claim 12, wherein the acoustic device comprises two or more receivers arranged at predetermined locations with respect to said at least one acoustic transceiver unit, the noise reduction module being configured and operable to analyze a combined output signal of said multiple receivers to thereby identify the acoustic signals from the outside of the region of interest.

14. The system of claim 12, wherein the noise reduction system comprises a cancellation module configured and operable to utilize input data indicative of characteristics of the predetermined acoustic signals and process data indicative of acoustic signals being received by applying thereto data corresponding to acoustic signals oppositely matching the characteristics of the predetermined acoustic signals.

15. The system of claim 14, wherein said cancellation module has one of the following configurations: (i) is configured as an analog circuit for applying said processing to the acoustic signals being received by the transceiver unit; and (ii) is configured as a digital processor for applying said processing to digital representation of the received acoustic signals.

16. The system of claim 1, wherein the control system comprises a noise reduction system comprising a cancellation module configured and operable to utilize input data indicative of characteristics of the predetermined acoustic signals and process data indicative of acoustic signals being received by applying thereto data corresponding to acoustic signals oppositely matching the characteristics of the predetermined acoustic signals.

17. The system of claim 9, wherein the extracted reflections of the predetermined acoustic signals from the region of interest are signals shifted from the predetermined acoustic signals in at least one of frequency and phase parameters.

18. The system of claim 1, wherein the analyzer module is in data communication with at least one of: (i) motion sensor device, which is configured and operable for sensing a movement profile of the subject and generating corresponding motion data, and (ii) an image acquisition device, which is configured and operable for visually monitoring a movement of the subject and generating image data indicative thereof.

19. The system of claim 1, further comprising an RF unit, the RF unit is configured for transmitting RF signals towards the subject and detect reflections therefrom and generate RF measured data based on the detected reflections;

wherein the control system is configured for communication with said RF unit to receive said RF measured data based indicative of reflections of RF signals from the subject; the analyzer is configured to analyze said RF measured data and determine an RF variation profile data indicative of a relation between the transmitted RF signal and the reflection thereof from the subject; and the extractor module is configured and operable to extract data indicative of the vital signs profile of the subject based on the acoustic variation profile data and the RF variation profile data.

20. The system of claim 1, wherein the control unit is configured for communication with a sound detector for receiving sound data indicative of sounds produced by the subject and the surrounding thereof; the control system comprising a sound analysis module configured to analyze said sound data and determine vital-signs-sound-based-data, the extractor is configured to extract the data indicative of the vital signs profile based on the acoustic variation profile data and the vital-signs-sound-based-data.

* * * * *